United States Patent [19]

Allais et al.

[11] 4,192,890

[45] Mar. 11, 1980

[54] NOVEL BENZOYLPHENYLACETIC ACID ESTERS

[75] Inventors: André Allais, Les Lilas; Jean Meier, Coeuilly-Champigny; Jacques Dube, Eaubonne, all of France

[73] Assignee: Roussel Uclaf, Paris, France

[21] Appl. No.: 15,786

[22] Filed: Feb. 28, 1979

Related U.S. Application Data

[60] Continuation of Ser. No. 621,162, Oct. 9, 1975, abandoned, which is a continuation of Ser. No. 299,636, Oct. 20, 1972, abandoned, which is a division of Ser. No. 133,429, Apr. 12, 1971, Pat. No. 3,741,988.

[30] Foreign Application Priority Data

Apr. 15, 1970 [FR] France ............................ 70.13579
Sep. 24, 1970 [FR] France ............................ 70.34591

[51] Int. Cl.$^2$ .................... A61K 31/215; C07C 69/95
[52] U.S. Cl. ........................................ 424/308; 560/9; 560/52
[58] Field of Search ........................ 560/52, 9; 424/308

[56] References Cited

U.S. PATENT DOCUMENTS

| | | | |
|---|---|---|---|
| 3,624,142 | 11/1971 | Shen et al. | 560/105 |
| 3,657,430 | 4/1972 | Shen et al. | 560/52 |
| 3,671,580 | 6/1972 | Shen et al. | 424/308 |
| 3,828,093 | 8/1974 | Bays et al. | 560/52 |

*Primary Examiner*—Jane S. Myers
*Attorney, Agent, or Firm*—Hammond & Littell, Weissenberger and Muserlian

[57] ABSTRACT

Racemates [and optically active isomers of benzoylphenylacetic acid esters of the formula

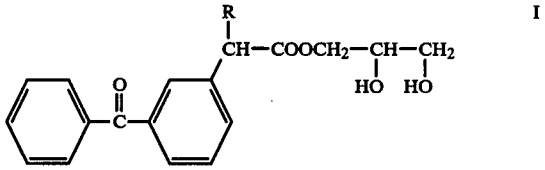

wherein R is selected from the group consisting of hydrogen and alkyl of 1 to 7 carbon atoms, and the two benzene rings may be optionally substituted with at least one member of the group consisting of chlorine, fluorine, bromine, trifluoromethyl and alkyl and alkoxy and alkylthio of 1 to 7 carbon atoms], intermediates and process for their preparation and their use as analgesics and antiinflammatory agents.

6 Claims, No Drawings

NOVEL BENZOYLPHENYLACETIC ACID ESTERS

PRIOR APPLICATION

This application is a continuation of copending U.S. patent application Ser. No. 621,162 filed Oct. 9, 1975, now abandoned, which in turn is a continuation of copending application Ser. No. 299,636 filed Oct. 20, 1972, now abandoned which is turn is a division of our copending application Ser. No. 133,429 filed Apr. 12, 1971 and now U.S. Pat. No. 3,741,988.

STATE OF THE ART

The literature describes certain derivatives of metabenzoylphenylacetic acids. French Pat. Nos. 1,516,775 and 1,546,478 and French Pat. BSM No. 6444 M describe metabenzoylphenyl acetic acids substituted or unsubstituted in one or the other aromatic ring or in the side chain. Belgian Pat. No. 718,466 describes the acids and derivatives of the carboxylic acid group such as alkyl esters, aryl esters aminoalkyl esters, amides and hydroxamic acids. These references teach that the said compounds possess anti-inflammatory activity about equal to phenyl butazone and analgesic activity.

However, no one has described the esterification of metabenzoylphenylacetic acids with polyhydroxy alcohols or their blocked derivatives. Glycerin esters or their blocked derivatives have been described for quinoleinic compounds in French Pat. No. 1,421,229 ($\alpha$-glycerin esters), in French Pat. BSM No. 5310 M ($\beta$-glycerin esters) and in French Pat. BSM No. 4775 M (blocked $\alpha$-glycerin esters in form of ketonides).

OBJECTS OF THE INVENTION

It is an object of the invention to provide the novel esters of formula I.

It is another object of the invention to provide novel intermediates and novel process for the preparation of the esters of formula I.

It is a further object of the invention to provide novel analgesic and anti-inflammatory compositions.

It is an additional object to provide a novel method of relieving pain and inflammation in warm-blooded animals.

These and other objects and advantages of the invention will become obvious from the following detailed description.

THE INVENTION

The novel compounds of the invention are racemates and optically active isomers of benzoylphenylacetic acid esters of the formula

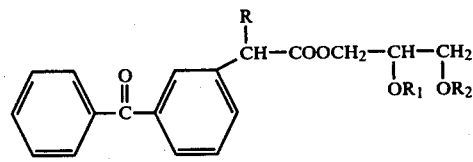

wherein R is selected from the group consisting of hydrogen and alkyl of 1 to 7 carbon atoms, $R_1$ and $R_2$ are hydrogen or taken together are

P and Q being alkyl of 1 to 5 carbon atoms and the two benzene rings may be optionally substituted with at least one member of the group consisting of chlorine, fluorine, bromine, trifluoromethyl and alkyl and alkoxy and alkylthio of 1 to 7 carbon atoms.

Preferred compounds of formula I are [4'-(2',2'-dimethyl-1',3'-dioxolanyl)] methanol esters of 3-p-chlorobenzoylphenylacetic acid, 3-p-chlorobenzoyl-2-methyl-phenylacetic acid and $\alpha$-(3-p-chlorobenzoylphenyl)-propionic acids and the glycerin mono-esters of 3-p-chlorobenzoylphenylacetic acid, 3-p-chlorobenzoyl-2-methyl-phenyl acetic acid and $\alpha$-(3-p-chlorobenzoylphenyl)-propionic acid.

The novel process for the preparation of the compounds of formula I comprises reacting an acid of the formula

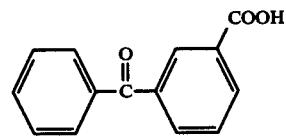

wherein the two benzene rings may be optionally substituted with at least one member of the group of chlorine, bromine, fluorine, —$CF_3$, lower alkyl, lower alkoxy, and lower alkylthio with a homologation agent and a dioxolane-4-methanol of the formula

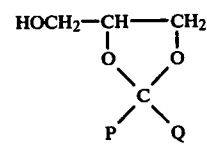

wherein P and Q have the above definition to obtain a corresponding ester of the formula

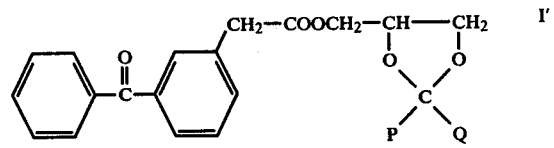

which may be $\alpha$-alkylated by treatment with a basic agent such as alkali metal hydrides, amides or dialkylamides then with alkylating derivative of the type R'X, R''SO$_3$R', ArSO$_3$R', and SO$_2$(OR')$_2$ wherein R' and R'' are lower alkyl, X is a halogen and Ar is an aromatic radical to form the corresponding ester of the formula

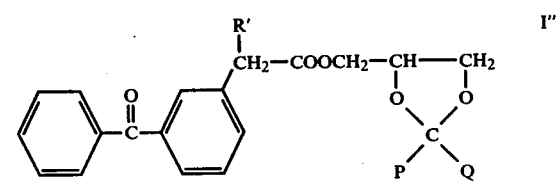

The compounds of formulae I' and I" can be hydrolyzed in the presence of an organic or mineral acid to form the corresponding ester of the formula

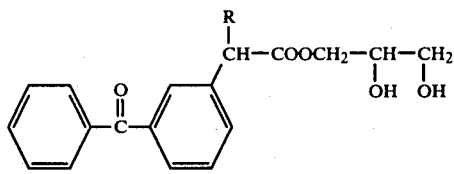

wherein R has the above definition.

The treatment with the homologation agent and dioxolane-4-methanol permits the direct conversion of the benzoic acid derivative to its higher esterified homolog. The method of homologation is the Arndt-Eistert method consisting principally of treating the benzoic acid of formula II with a chlorination agent to form the corresponding acid chloride which is then reacted with diazomethane to form the diazoketone which rearranges in the presence of a silver derivative such as silver oxide or silver benzoate with the last step being effected in the presence of a dioxolane-4-methanol to obtain the ester of formula I'.

The decomposition of the diazoketone is preferably effected with silver benzoate in solution in a tertiary amine such as triethylamine and the diazoketone in solution in dioxolane-4-methanol of formula III.

The α-alkylation step is preferably effected by reacting the ester of formula I' with a lithium dialkylamide such as lithium diethylamide in a mixture of solvents with a strong dielectric constant such as hexamethylphosphortriamide and tetrahydrofuran and the reaction product is then reacted with an alkyl iodide. Other basic agents such as sodium hydride or sodium amide and other organic media such as dimethylformamide or an ether-benzene mixture may also be used.

The hydrolysis of the ester of formula I' or I" may be effected with a mineral acid such as hydrochloric acid, sulfuric acid, perchloric acid, boric acid, etc., or an organic acid such as acetic acid, trichloroacetic acid, formic acid, trifluoroacetic acid, etc.

The substituted benzoic acids of formula II used as the starting materials can be prepared by the process of Belgian Pat. No. 718,466 by hydrogenating m-nitrobenzophenone with hydrogen in the presence of a catalyst and then subjecting the reaction product to the Sandmeyer reaction to form m-cyano-benzophenone which is hydrolyzed to the corresponding acid of formula II.

A preferred process for the preparation of 3-p-chlorobenzoyl-2-methyl-benzoic acid comprises reacting p-chlorophenyl lithium with 2-methyl-3-cyano-benzoic acid and hydrolyzing the imine formed to obtain the desired acid. In a variation of the process, 2-methyl-3-cyano-benzoyl chloride is reacted with p-chlorophenyl cadmium to obtain 3-p-chlorobenzoyl-2-methyl-benzonitrile which is hydrolyzed to form the desired acid. The said processes can be used to prepare other compounds of formula II.

In a variation of the process to obtain an ester of formula I, the process comprises reacting a benzoic acid of the formula

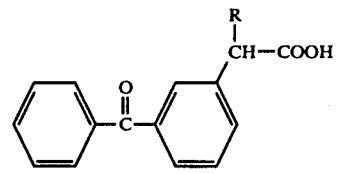

with an esterification agent of an alkyl of 1 to 3 carbon atoms to form the ester of the formula

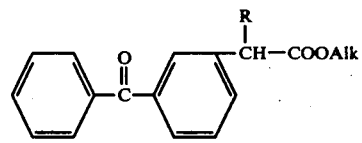

wherein R has the above meaning and Alk is alkyl of 1 to 3 carbon atoms, subjecting the said ester to transesterification in the presence of an alkaline agent with a dioxolane-4-methanol of the formula

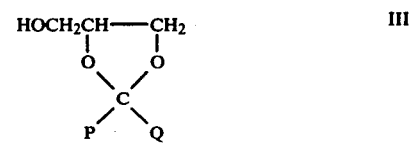

wherein P and Q have the above definitions to form the corresponding ester of the formula

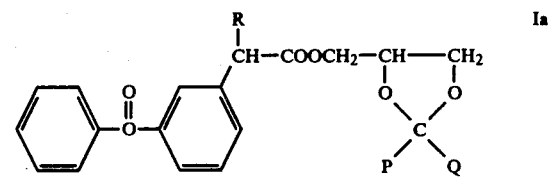

which if desired can be hydrolyzed with an organic or mineral acid to form the corresponding polyol ester.

The alkaline agent for the transesterification is preferably an alkali metal such as sodium, an alkali metal alcoholate such as sodium ethylate, an alkali metal hydride or an alkali metal amide. The preferred agent is sodium hydride. The acids for the hydrolysis may be the same as discussed above.

The acids of formula IV can be prepared by a process wherein 3-methyl-benzophenone is reacted with a brominating agent to form 3-bromomethyl-benzophenone, the latter is reacted with an alkali metal cyanide to form m-benzoylphenylacetonitrile which can be hydrolyzed to the corresponding acid or reacted with an alkylating agent in in the presence of sodium hydride to form a meta-benzoyl-α-alkylphenylacetonitrile which is then hydrolyzed to the corresponding phenylacetic acid.

The novel anti-inflammatory and analgesic compositions of the invention are comprised of an effective amount of at least one ester of formula I and a pharmaceutical carrier. The compositions may be in the form of injectable solutions or suspensions in ampoules, multiple dose flacons or antoinjectable syringes, or in the form of tablets, coated tablets, gelules, sublingual tablets, syrups, emulsions, suppositories, granules, aromatic powders, creams, pomades, gels, drops or powders.

The compositions usually contain 5 to 200 mg of the active compound of formula I depending upon the specific compound and the method of administration. The compositions may also contain other active principles such as spasmolytics, anticoagulants, antipyretics or sedatives.

The compositions are useful for the treatment of arthroses, lombulgia, sciatic, sore shoulders, myalgia or permits the reeducation of muscles. The compositions soothe aches, increase articular movements, increase the rate of perimeter of step and struggle against ankylosis and inflammation. The esters of formula I have a much higher anti-inflammatory activity than the corresponding free acids while having the same degree of analgesic activity as the free acids. Notwithstanding the very sensible increase in the anti-inflammatory activity of the esters in relation to the corresponding acids, the ulcergenic properties possessed by most anti-inflammatory products is of the same or a lesser order resulting in an important improvement of the margin of safety. The analgesic properties of the ketonides of formula I are superior to known analgesics such as indomethacine, niflumic acid or phenylbutazone.

The novel method of the invention for relieving pain and inflammation in warm-blooded animals comprises administering to warm-blooded animals an effective amount of at least one compound of formula I. The compounds may be administered orally, transcutaneously, rectally, perlingually, topically or transmucously. The usual daily dose is 0.15 to 15 mg/kg depending upon the compound and the method of administration.

In the following examples there are described several preferred embodiments to illustrate the invention. However, it should be understood that the invention is not intended to be limited to the specific embodiments.

EXAMPLE I

PREPARATION OF
[4'-(2',2'-dimethyl-1',3'-dioxolanyl)] methyl
α-(3-p-chlorobenzoyl phenyl) propionate STEP A: 3-p-chlorobenzoyl-benzonitrile 30 g of magnesium turnings in 400 cc of ether were heated to reflux and then a solution of 190 g of p-bromochloro-benzene in 600 cc of ether was added over one hour after which the mixture was refluxed for 1½ hours to obtain a solution titrating 0.77 mole of magnesium compound per liter. 31.4 g of cadmium chloride (dried at 140° C.) were added over 15 minutes to 450 cc of the said magnesium solution at 15° C. and after stirring for 1 hour at room temperature the ether was eliminated by distillation while progressively replacing the same with benzene to maintain a constant volume. The resulting solution was cooled to 5° C. and a solution of 54.5 g of 3-cyano-benzoic acid chloride [Slotta et al, Ber., Vol 71 (1938), p. 335–41] in 300 cc of benzene was added thereto over 30 minutes. The mixture was stirred for 15 hours at room temperature and then refluxed for 3 hours. After cooling to 10° C., an aqueous solution of 2.5% hydrochloric acid was added thereto and the organic phase was decanted off. The aqueous phase was extracted with methylene chloride and the organic phases were combined, successively washed with aqueous 2 N hydrochloric acid solution, water, aqueous 2 N sodium hydroxide solution and water, dried, treated with activated carbon, stirred and filtered. The filtrate was evaporated to dryness under reduced pressure and the residue was empasted with isopropyl ether and dried to obtain 47.5 g of 3-p-chlorobenzoyl-benzonitrile melting at 142° C. A sample of the product after crystallization from methanol melted at 142° C.

| Analysis: | $C_{14}H_8NClO$; molecular weight = 241.68 | | | |
|---|---|---|---|---|
| Calculated: | %C 69.58 | %H 3.33 | %N 5.79 | %Cl 14.67 |
| Found: | 69.2 | 3.3 | 5.9 | 14.5 |

As far as is known, this compound is not described in the literature.

STEP B: 3-p-chlorobenzoyl-benzoic acid 46.5 g of 3-p-chlorobenzoyl benzonitrile were added to a mixture of 350 cc of water, 350 cc of glacial acetic acid and 350 cc of concentrated sulfuric acid and the resulting mixture was refluxed for 3 hours and 40 minutes. After cooling to 10° C., the mixture was slowly added to water and the precipitate formed was recovered by vacuum filtration, was washed and dried to obtain 48 g of 3-p-chlorobenzoyl benzoic acid melting at 228° C. A sample of the product after crystallization from acetone melted at 234° C.

| Analysis: | $C_{14}H_9 Cl O_3$; molecular weight = 260.63 | | |
|---|---|---|---|
| Calculated: | %C 64.50 | %H 3.48 | %Cl 13.60 |
| Found: | 64.2 | 3.4 | 13.7 |

As far as is known, this compound is not described in the literature.

STEP C: [4'-(2',2'-dimethyl-1',3'-dioxolanyl)] methyl 3-p-chloro benzoyl phenyl acetate 47 g of 3-p-chloro benzoyl-benzoic acid were added to 470 cc of thionyl chloride and the mixture was refluxed for 3 hours and then cooled to 20° C. The mixture was concentrated to dryness by distillation under reduced pressure to obtain a residue of 3-p-chlorobenzoyl-benzoic acid chloride which as far as is known is not described in the literature. 54.8 gm of the said acid chloride were added to 500 cc of methylene chloride and after cooling to 5° C., 1.5 liters of a solution of 15.2 g per liter of diazomethane in methylene chloride was added thereto over 20 minutes.

The mixture was stirred for 15 hours at 20° C. and was concentrated to dryness by distillation under reduced pressure to obtain the corresponding diazoketone which as far as is known, is not described in the literature. The said diazoketone was suspended in 350 cc of 4-(2,2-dimethyl-1,3-dioxolane)-methanol and then a solution of 9 g of silver benzoate in 112.5 cc of triethylamine was added dropwise at 36° C. in six hours. The product gave off nitrogen and after cooling to 20° C., it was added to water. The insoluble was removed by filtration and the insoluble and the aqueous phase were reextracted with ether. The ether phase was washed with water, dried, treated with activated carbon which was filtered off and evaporated to dryness under reduced pressure. The residue was purified by passage over silica gel and elution with a 95:5 mixture of methylene chloride and ether. The eluate was treated with activated carbon and concentrated to dryness under reduced pressure to obtain 39.73 g of [4'-(2',2'-dimethyl-1',3'-dioxolanyl)]methyl 3-p-chlorobenzoylphenyl acetate melting at 70° C.

| Analysis: | $C_{21}H_{21}ClO_5$; molecular weight = 388.83 | | |
|---|---|---|---|
| Calculated: | %C 64.87 | %H 5.44 | %Cl 9.11 |
| Found: | 64.8 | 5.4 | 9.2 |

As far as is known, this compound is not described in the literature.

STEP D: [4'-(2',2'-dimethyl-1',3'-dioxolanyl)] methyl α-(3-p-chlorobenzoylphenyl) propionate 15 cc of a solution of 1.7 moles of butyllithium per liter of hexane was added over 20 minutes while keeping the temperature below $-35°$ C. to a mixture of 100 cc of tetrahydrofuran, 100 cc of hexamethyl phosphor triamide and 2.65 cc of diethylamine cooled to $-40°$ C. and the mixture was then stirred for 15 minutes at $-40°$ C. A solution of 10 g of [4'-(2',2'-dimethyl-1',3'-dioxolane)]methyl 3-p-chlorobenzoyl phenyl acetate in 60 cc of tetrahydrofuran was added thereto over 15 minutes while keeping the temperature below $-35°$ C. and the mixture was then stirred for 15 minutes at $-40°$ C. After the addition of 3.5 cc of methyl iodide, the mixture was stirred for 30 minutes at $-35°$ C. and then allowed to stand at $20°$ C. for 1 hour. The mixture was added to water and the aqueous phase was extracted with isopropyl ether. The ether phase was washed with water, dried and concentrated to dryness under reduced pressure. The residue was dissolved in ethyl ether and the solution was treated with activated carbon which was removed by filtration. The filtrate was evaporated to dryness under reduced pressure to obtain 9.8 g of [4'-(2',2'-dimethyl-1',3'-dioxolanyl)]-methyl α-(3-p-chlorobenzoyl phenyl)-propionate

| Analysis: | $C_{22}H_{23}ClO_5$; molecular weight = 402.87 | | |
|---|---|---|---|
| Calculated: | %C 65.59 | %H 5.75 | %Cl 8.80 |
| Found: | 65.3 | 5.8 | 9.1 |

As far as is known, this compound is not described in the literature.

EXAMPLE II

PREPARATION OF
2',3'-dihydroxypropyl α-(3-p-chloro benzoyl phenyl) propionate 6.97 g of [4'-(2',2'-dimethyl-1',3'-dioxolanyl)]methyl α-(3-p-chlorobenzoyl phenyl) propionate and 10.8 g of boric acid were added to 35 cc of methoxy ethanol and the reaction mixture was heated at 100° C. for 2 hours. The mixture was cooled to 10° C. and was filtered to remove the boric acid that precipitated and was washed with ether. The organic phase was washed with water, a saturated aqueous sodium bicarbonate solution and with water and dried. The solution was treated with activated carbon and was concentrated to dryness by distillation under reduced pressure to obtain 5.87 g of the 2',3'-dihydroxy-propyl α-(3-p-chlorobenzoyl phenyl) propionate.

| Analysis: | $C_{19}H_{19}ClO_5$; molecular weight = 362.81 | | |
|---|---|---|---|
| Calculated: | %C 62.90 | %H 5.27 | %Cl 9.77 |
| Found: | 62.9 | 5.2 | 9.8 |

As far as is known, this compound is not described in the literature.

EXAMPLE III

PREPARATION OF
[4'-(2',2'-dimethyl-1',3'-dioxolanyl)]methyl 3-p-chlorobenzoylphenyl acetate STEP A: 3-bromomethyl-4'-chlorobenzophenone A mixture of 68 g of m-toluic acid and 107.5 g of phosphorus pentachloride was kept in contact for 15 minutes and the phosphorous oxychloride formed was distilled off under reduced pressure. Then 112.5 g of chlorobenzene were added thereto and the mixture was heated to 90° to 100° C. with stirring. Then, 66.75 g of aluminum chloride were added to the mixture which was stirred for 2 hours at 125°–135° C. After cooling to room temperature, 300 g of ice were added to the mixture which was then vacuum filtered. The recovered precipitate was empasted with water and dried under reduced pressure. The residue was crystallized from methanol, treated with activated carbon, and dried under reduced pressure to obtain 67.1 g of 3-methyl-4'-chlorobenzophenone melting at 108° C.

A mixture of 23.05 g of 3-methyl-4'-chlorobenzophenone, 70 cc of carbon tetrachloride, 16.02 g of N-bromosuccinimide and 90 mg benzoyl peroxide was refluxed for 4 hours and then was added to 100 cc of carbon tetrachloride. The mixture was filtered hot and the filter was washed with 100 cc of boiling carbon tetrachloride. 200 cc of the solvent were distilled off under reduced pressure and the mixture was cooled and iced for 1 hour. The mixture was vacuum filtered and the recovered crystals were empasted with iced carbon tetrachloride and dried under reduced pressure. The residue was crystallized from ethanol to obtain 17.5 g of 3-bromomethyl-4'-chlorobenzophenone melting at 138°–139° C.

STEP B: 3-p-chlorobenzoylphenyl-acetonitrile

A solution of 17 g of 3-bromomethyl-4'-chlorobenzophenone in 75 cc of dioxane at 70° C. was added to the solution of 26.5 g of potassium cyanide in 75 cc of water and the mixture was refluxed with stirring for 6 hours. After cooling, 500 cc of ether were added to the mixture and the aqueous phase was decanted off. The organic phase was washed with water until the wash waters were neutral, dried over magnesium sulfate, treated with activated carbon, filtered and evaporated to dryness under reduced pressure. The residue was crystallized from methanol to obtain 9.61 g of 3-p-chlorobenzoyl phenyl acetonitrile melting at 86° to 90° C.

STEP C: 3-p-chlorobenzoyl phenyl-acetic acid

A mixture of 9.61 g of 3-p-chlorobenzoyl phenyl acetonitrile, 75 cc of water, 75 cc of acetic acid and 75 cc of sulfuric acid was refluxed with stirring for 2½ hours and then cooled and iced for 1 hour. The mixture was vacuum filtered and the precipitate was empasted with water and taken up in 50 cc of a 10% aqueous sodium carbonate solution. The solution was filtered and the filter was washed with water. The pH of the filtrate was adjusted to 5–6 by addition of acetic acid and after being iced for 30 minutes, the mixture was vacuum filtered. The recovered precipitate was washed with water and dried under reduced pressure. The residue was dissolved in 50 cc of refluxing toluene and the solution was treated with activated carbon and filtered. The filter was washed with boiling toluene. The filtrate was cooled and iced for 1 hour and then vacuum filtered. The recovered precipitate was empasted with iced toluene and dried under reduced pressure to obtain 8.37 g of 3-p-chlorobenzoyl phenyl-acetic acid melting at 148° C.

STEP D: Methyl 3-p-chlorobenzoyl phenylacetate 10.3 g of 3-p-chlorobenzoyl phenylacetic acid were dissolved in 250 cc of methylene chloride and a solution of diazomethane in methylene chloride was added thereto until there was a yellow coloration. The reaction mixture was stirred for 30 minutes and then a few drops of acetic acid were added to destroy any excess diazomethane. The organic phase was washed with iced 0.1 N sodium hydroxide solution and then with water until the wash waters were neutral, dried over sodium sulfate, treated with activated carbon, filtered and dried. The residue was empasted with isopropyl ether filtered and dried to obtain 7.5 g of methyl 3-p-chlorobenzoyl phenylacetate. The product occurred in the form of a colorless solid melting at 65° C. and soluble in most of the usual organic solvents and insoluble in water. Crystallization of the product from isopropyl ether for analysis did not change the melting point.

| Analysis: | $C_{16}H_{13}Cl\ O_3$; molecular weight = 280.72 | | |
|---|---|---|---|
| Calculated: | %C 66.56 | %H 4.54 | %Cl 12.28 |
| Found: | 66.3 | 4.6 | 12.5 |

As far as is known, this compound is not described in the literature.

STEP E: [4'-(2',2'-dimethyl-1',3'-dioxolanyl)]methyl 3-p-chlorobenzoyl-phenylacetate 40 cc of 4-(2,2-dimethyl-1,3-dioxolane) methanol heated to 85° C. was added to 0.20 g of a suspension of 50% sodium hydride in vaseline oil and 5.774 g of methyl 3-p-chlorobenzoyl-phenylacetate and the reaction mixture was stirred for 3 hours at 85° C. under a pressure of 30 mm Hg. The reaction mixture was then added to 100 cc of water containing a few drops of acetic acid and the mixture was extracted with ether. The ether phase was dried over magnesium sulfate and was evaporated to dryness under reduced pressure. The residue was subjected to chromatography over magnesium silicate to obtain a 65% yield of [4'-(2',2'-dimethyl-1',3'-dioxolanyl)]methyl 3-p-chlorobenzoyl-phenylacetate in the form of a crystalline product melting at 70° C. The product was soluble in methylene chloride, chloroform, methanol, acetone and ethyl ether.

| Analysis: | $C_{21}H_{21}Cl\ O_5$; molecular Weight = 388.85 | | |
|---|---|---|---|
| Calcuated: | %C 64.87 | %H 5.44 | %Cl 9.11 |
| Found: | 64.6 | 5.4 | 9.4 |

The product was identical to that described in Step C of Example I.

EXAMPLE IV

PREPARATION OF 2',3'-dihydroxypropyl 3-p-chlorobenozylphenylacetate

A mixture of 3.292 g of [4'-(2',2'-dimethyl-1',3',-dioxolanyl)]methyl 3-p-chloro-benzoyl phenyl acetate, 5.231 g of boric acid and 17 cc of methoxyethanol was heated at 100° C. for 45 minutes and after cooling, the mixture was vacuum filtered. The filtrate was added to 200 cc of water and the mixture was extracted with ether. The ether phase was washed with an aqueous sodium bicarbonate solution, dried over magnesium sulfate and evaporated to dryness under reduced pressure. The residue was empasted with isopropyl ether and then crystallized from ethyl ether to obtain a 70% yield of 2',3'-dihydroxypropyl 3-p-chlorobenzoyl phenyl acetate melting at 68° C. The colorless product was soluble in methylene chloride, chloroform, methanol, ethyl ether and acetone.

| Analysis: | $C_{18}H_{17}Cl\ O_5$; molecular weight = 350.78 | | |
|---|---|---|---|
| Calculated: | %C 61.99 | %H 4.91 | %Cl 10.17 |
| Found: | 61.8 | 4.9 | 10.5 |

IR Spectrum:

Presence of ester, conjugated ketone, aromatic substituted with a heteroatom—and —OH.

As far as is known, this product is not described in the literature.

EXAMPLE V

PREPARATION OF [4'-(2',2'-dimethyl-1',3'-dioxolanyl)]methyl 3-p-chlorobenzoyl-2-methyl phenyl acetate STEP A: 3-cyano-2-methyl-benzoyl chloride 75 cc of thionyl chloride and 30 g of 3-cyano-2-methyl-benzoic acid [prepared by process in C. R. Acad. Sci., Vol. 235(1952), p. 1660] were refluxed for 1½ hours and after cooling, excess thionyl chloride was removed under reduced pressure. The last traces of thionyl chloride were removed by addition of benzene and distillation under reduced pressure. The residue was purified by rectification under reduced pressure to obtain 27.4 g of 3-cyano-2-methyl-benzoyl chloride in the form of colorless crystals melting at 62° C.

| Analysis: | $C_9H_6NCl\ O$; molecular weight = 179.60 | | | | | | |
|---|---|---|---|---|---|---|---|
| Calculated: | %C | 60.19 | %H | 3.36 | %N 7.80 | %Cl | 19.74 |
| Found: | | 60.0 | | 3.2 | 8.1 | | 19.4 |

As far as is known, this product is not described in the literature.

STEP B: 3-p-chlorobenzoyl-2-methyl-benzoic acid

A solution of 95 g of p-bromochlorobenzene in 250 cc of ether was added to 15 g of magnesium in 250 cc of ether while maintaining the reaction mixture at reflux. The mixture was stirred for 1½ hours at room temperature to obtain a solution containing 0.78 mole per liter of p-chlorophenyl magnesium bromide. 17.9 g of cadmium chloride were added to 230 cc of the acid solution and after stirring for 10 minutes, the ether was distilled off while maintaining the volume constant by addition of benzene to obtain a benzene solution of bis-(p-chlorobenzene) cadmium compound.

The said benzene solution was cooled to 5° C. and then a solution of 27.4 g of 3-cyano-2-methyl-benzoyl chloride in 85 cc of benzene was added thereto. The mixture was allowed to return to room temperature and was stirred overnight. The mixture was refluxed for 3½ hours and after cooling, the mixture was added to a solution of 30 cc of hydrochloric acid in 600 cc of water. The mixture was extracted with ether and the combined ether phases were washed successively with 1 N hydrochloric acid, water, 1 N sodium hydroxide and water until the wash waters were neutral. The organic phase was dried over magnesium sulfate and evaporated to dryness under reduced pressure. The residue was empasted with 40 cc of petroleum ether, vacuum filtered, washed with petroleum ether and dried at room temperature under reduced pressure to obtain 30.6 g of 3-p-chlorobenzoyl-2-methyl-benzonitrile. For analysis, the product was crystallized from methanol and melted at 84° C. The compound occurred in the form of beige crystals soluble in methylene chloride and chloroform.

| Analysis: | $C_{15}H_{10}NClO$; molecular weight = 255.70 | | | | | | | |
|---|---|---|---|---|---|---|---|---|
| Calculated: | %C | 70.46 | %H | 3.94 | %N | 5.47 | %Cl | 13.87 |
| Found: | | 70.3 | | 3.8 | | 5.5 | | 13.5 |

IR Spectrum:
Presence of C≡N at 2227 cm$^{-1}$
As far as is known, this compound is not described in the literature.

STEP C: 3-p-chlorobenzoyl-2-methyl-benzoic acid

A mixture of 28 g of 3-p-chlorobenzoyl-2-methyl-benzonitrile, 210 cc of glacial acetic acid, 210 cc of water and 210 cc of concentrated sulfuric acid was refluxed overnight and after cooling to 80° C., the reaction mixture was added to a water-ice mixture. The mixture was vacuum filtered and the resulting precipitate was washed with water until the wash waters were neutral and then dried under reduced pressure to obtain 29.9 g of 3-p-chlorobenzoyl-2-methyl-benzoic acid melting at 205° C. The product was soluble in ethanol and chloroform and slightly soluble in ethyl ether. After crystallization from methanol for analysis, the product melted at 206° C.

| Analysis: | $C_{15}H_{11}O_3Cl$; molecular weight = 274.69 | | |
|---|---|---|---|
| Calculated: | %C 65.58 | %H 4.03 | %Cl 12.91 |
| Found: | 65.7 | 4.0 | 13.0 |

IR Spectrum:
Absence of C≡N and presence of carbonyl at 1689 and 1672 cm$^{-1}$ and aromatic.
As far as is known, this product is not described in the literature.

STEP D: [4-(2',2'-dimethyl-1',3'-dioxolanyl)]methyl 3-p-chlorobenzoyl-2-methyl-phenylacetate A mixture of 29.9 g of 3-p-chlorobenzoyl-2-methyl-benzoic acid and 300 cc of thionyl chloride was refluxed for 3 hours and then stirred at room temperature overnight. Excess thionyl chloride was removed under reduced pressure and the last traces were eliminated by adding benzene and distilling the benzene off under reduced pressure to obtain 3-p-chlorobenzoyl-2-methyl-benzoyl chloride.

As far as is known, this compound is not described in the literature. A mixture of ⅓ of the said benzoyl chloride and 100 cc of methylene chloride was cooled to 10° C. and 300 cc of a methylene chloride solution containing 12.15 g per liter of diazomethane were added thereto.

The mixture was stirred overnight at room temperature and the methylene chloride was distilled off to obtain the corresponding diazoketone which, as far as is known, is not described in the literature.

The said diazoketone was dissolved in 100 cc of 4-(2,2-dimethyl-1,3-dioxolane)-methanol and then 7 cc of a solution of 1 g of silver benzoate in 12.5 cc of triethylamine was added thereto in small fractions with stirring at room temperature. After the evolution of nitrogen eased, the reaction mixture was added to water and was extracted with ether. The ether phase was washed with a saturated aqueous sodium bicarbonate solution and then with water until the wash waters were neutral. The ether solution was dried over magnesium sulfate, treated with activated carbon, filtered and evaporated to dryness under reduced pressure. The residue was purified by passage over magnesium silicate and elution with ether. The solvent was evaporated off under reduced pressure to obtain 8.2 g of [4'-(2',2'-dimethyl-1',3'-dioxolanyl)]methyl 3-p-chlorobenzoyl-2-methyl-phenylacetate in the form of a pale yellow, amorphous product soluble in chloroform and methanol and insoluble in water.

| Analysis: | $C_{22}H_{23}ClO_5$; molecular weight = 402.87 | | |
|---|---|---|---|
| Calculated: | %C 65.59 | %H 5.75 | %Cl 8.80 |
| Found: | 65.8 | 5.9 | 8.8 |

IR Spectrum: (Chloroform)
Presence of ester carbonyl at 1741 cm$^{-1}$, conjugated ketone at 1668 cm$^{-1}$, aromatic and ketal.
As far as is known, this compound is not described in the literature.

EXAMPLE VI

PREPARATION OF 2',3'-dihydroxypropyl 3-p-chlorobenzoyl-2-methyl-phenylacetate

A mixture of 7.6 g of [4'-(2',2'-dimethyl-1'-,3'-dioxolanyl)]methyl 3-p-chlorobenzoyl-2-methyl-phenylacetate, 12 g of boric acid and 54.5 cc of methoxy ethanol was heated at 100° C. for 1¼ hours and then was cooled and filtered. The filtrate was added to 300 cc of water and the mixture was extracted with ether. The ether extracts were washed with aqueous sodium bicarbonate solution and then with water until the wash waters were neutral. The ether solution was then dried over magnesium sulfate and evaporated to dryness under reduced pressure. The residue was purified by passage through magnesium silicate and elution with ether which was evaporated off under reduced pressure to obtain 5.63 g of 2',3'-dihydroxypropyl 3-p-chlorobenzoyl-2-methyl-phenylacetate in the form of an amorphous yellow solid soluble in chloroform, ether and methanol and insoluble in water.

| Analysis: | $C_{19}H_{19}ClO_5$; molecular weight = 362.81 | | |
|---|---|---|---|
| Calculated: | %C 62.90 | %H 5.28 | %Cl 9.77 |
| Found: | 63.1 | 5.3 | 9.7 |

IR Spectrum: (Chloroform):
Presence of ester at 1741 cm$^{-1}$, of conjugated ketone at 1668 cm$^{-1}$ and aromatic and OH.
As far as is known, this product is not described in the literature.

EXAMPLE VII

PREPARATION OF 3-p-chlorobenzoyl-2-methyl-benzoic acid

A solution of 68 g of p-chlorobromobenzene in 150 cc of ether was added under an inert atmosphere to 250 cc of a solution of 1.4 N butyl lithium in hexane cooled to −20° C. and after stirring for 2 hours, the temperature was allowed to rise to room temperature. A solution of 28.6 g of 3-cyano-2-methylbenzoic acid in 300 cc of tetrahydrofuran was added to the solution of the lithium compound cooled to −60° C. and then the temperature was allowed to return to room temperature and remain there overnight. The reaction mixture was added to a water-ice mixture and made acidic by addition of hydrochloric acid. The mixture was heated at 70°–80° C. for 3 hours and the tetrahydrofuran was distilled off. After cooling, the mixture was extracted with ether and the ether phase was washed with water, dried over magnesium sulfate and concentrated. The residue was empasted with isopropyl ether, vacuum filtered and dried. The residue was crystallized from methanol, and dissolved in methanol and treated with activated carbon, concentrated and allowed to crystallize to obtain 10.3 g of 3-p-chlorobenzoyl-2-methyl-benzoic acid melting at 206° C. A second crop of 4.3 g of product was obtained by crystallization of the mother liquors.

PHARMACOLOGICAL DATA

Inflammation Test of the Paw of a Rat Caused by Naphthoylheparamine

The test used was that of D. Branceni et al. (Arch. Int. Pharmacodynamie 1954, 152, 15). It consists in administering to rats of about 150 gm weight in a single injection 1 mg of naphthoylheparamine under the plantar aponeurosis of a hind paw of the rat, which provoked an inflammatory edema. The test products are orally administered in solution or in an aqueous suspension one hour before the irritant injection.

The degree of inflammation is estimated by plethysmometry with an electric plethysmometric. The volume of the paw is expressed in arbitrary units. It is measured immediately before and two hours after the injection of naphthoylheparamine. The increase in paw volume between the two measurements was the degree of inflammation. The degree of average inflammation for each group is expressed in absolute values and as a percentage of the control animals. The $DA_{40}$ or dose for reducing the degree of inflammation by 40% of that of the controls was determined. The doses and results for the compounds are reported in the following tables.

TABLE A

2',3'-dihydroxypropyl 3-p-chlorobenzyl-phenylacetate

| Lots | Doses Administered in mg/kg | Increase in volume of paw | % of Protection |
|---|---|---|---|
| Controls | 0 | 17.1 | — |
| Treated | 10 | 7.0 | 59 |
| Controls | 0 | 18.6 | — |
| Treated | 1 | 12.1 | 35 |
|  | 5 | 8.4 | 55 |

TABLE B

2',3'-dihydroxypropyl 3-p-chlorobenzoyl-2-methyl-phenylacetate

| Lots | Doses Administered in mg/kg | Increase in volume of paw | % of Protection |
|---|---|---|---|
| Controls | 0 | 18.1 | — |
| Treated | 2.5 | 9.8 | 46 |
|  | 5 | 7.1 | 61 |

TABLE C

[4'-(2',2'-dimethyl-1',3'-dioxolanyl)]-methyl 3-p-chlorobenzoyl 2-methyl-phenylacetate

| Lots | Doses Administered in mg/kg | Increase in volume of paw | % of Protection |
|---|---|---|---|
| Control | 0 | 18.4 | — |
| Treated | 1 | 8.9 | 52 |
| Controls | 0 | 26.6 | — |
| Treated | 250 γ/kg | 15.5 | 42 |
|  | 500 γ/kg | 10.9 | 59 |

TABLE D

2',3'-dihydroxy-propyl α-(3-p-chlorobenzoylphenyl)-propionate

| Lots | Doses Administered in mg/kg | Increase in volume of paw | % of Protection |
|---|---|---|---|
| Controls | 0 | 30.3 | — |
| Treated | 1 | 24.1 | 21 |
|  | 5 | 18.1 | 40 |
| Control | 0 | 22.4 | — |
| Treated | 10 | 10.6 | 53 |

TABLE E

[4'-(2',2'-dimethyl-1',3'-dioxolanyl)]-methyl α-(3-p-chlorobenzoylphenyl)-propionate

| Lots | Doses Administered in mg/kg | Increase in Vomume of paw | % of Protection |
|---|---|---|---|
| Control | 0 | 26.1 | — |
| Treated | 1 | 20.4 | 22 |
|  | 5 | 15.1 | 42 |
|  | 10 | 10.0 | 61 |

The $DA_{40}$ for 2',3'-dihydroxypropyl 3-p-chlorobenzoylphenylacetate is 1.5 mg/kg, for 2',3'-dihydroxypropyl 3-p-chlorobenzoyl-2-methyl-phenylacetate is 2 mg/kg, for [4'-(2',2'-dimethyl-1',3'-dioxolanyl)] methyl 3-p-chlorobenzoyl-2-methylphenylacetate is 250 γ/kg, and for 2',3'-dihydroxypropyl α-(3-p-chlorobenzoylphenyl)-propionate and for [4'-(2',2'-dimethyl-1',3'-dioxolanyl)] methyl α-(3-p-chlorobenzoylphenyl)propionate are 5 mg/kg. These results show that the 5 compounds have an important anti-inflammatory activity.

B. Analgesic Effect

The test used was based on the fact noted by R. Koster et al. (Fed. Proc., 1959, Vol. 18, page 412) wherein the intraperitoneal injection of acetic acid causes in mice characteristic repeated stretching and twisting movements which can persist for more than six hours. Analgesics prevent or suppress this syndrome which, therefore, can be considered as externalization of a diffuse abdominal pain.

A solution of 0.6% acetic acid in water containing 10% arabic gum was used and the dose which released the syndrome under these conditions was 0.01 cc/gm, that is 60 mg/kg of acetic acid. The test compounds were administered orally one-half hour before the intraperitoneal injection of acetic acid, the mice having fasted since the night before the experiment. For each dose and for each control, which are obligatory for each test, a group of 5 animals was used. For each mouse, the stretchings were observed and counted and then added for the group of 5 during a period of 15 minutes starting immediately after the injection of acetic acid.

The following table summarizes the doses and the results.

TABLE A'

2',3'-dihydroxypropyl 3-(p-chlorobenzoyl)-phenylacetate

| Doses Administered in mg/kg | % of Protection |
| --- | --- |
| 5 | 49 |
| 10 | 70 |
| 20 | 60 |
| 50 | 78 |

TABLE B'

2',3'-dihydroxy-propyl 3-p-chlorobenzoyl -2-methyl-phenyl-acetate

| Doses Administered in mg/kg | % of Protection |
| --- | --- |
| 1 | 47 |
| 2 | 33 |
| 5 | 57 |
| 10 | 73 |
| 20 | 80 |

TABLE C'

[4'-(2',2'-dimethyl 1',3'-dioxolanyl)]methyl 3-(p-chlorobenzoyl) 2-methylphenylacetate

| Doses Administered in mg/kg | % of Protection |
| --- | --- |
| 1 | 19 |
| 2 | 50 |
| 5 | 48 |
| 10 | 66 |
| 20 | 83 |
| 50 | 85 |

TABLE D'

2',3'-dihydroxy-propyl α-(3-p-chlorobenzoylphenyl)-propionate

| Doses administered | % of protection |
| --- | --- |
| 50 γ/kg | 16 |
| 100 γ/kg | 29 |
| 200 γ/kg | 53 |
| 500 γ/kg | 66 |
| 1 mg/kg | 84 |

TABLE E'

[4'-(2',2'-dimethyl-1',3'-dioxolanyl)]methyl α-(3-p-chloro-benzoylphenyl)-propionate

| Doses administered in mg/kg | % of protection |
| --- | --- |
| 1 | 32 |
| 2 | 56 |
| 5 | 81 |

The $DA_{50}$ for 2',3'-dihydroxypropyl 3-p-chlorobenzoylphenylacetate was 5 mg/kg, for 2',3'-dihydroxypropyl 3-p-chlorobenzoyl-2-methyl-phenylacetate and for [4'-(2',2'-dimethyl-1',3'-dioxolanyl)] methyl 3-p-chlorobenzoyl-2-methylphenylacetate is between 2 and 5 mg/kg, for 2',3'-dihydroxypropyl α-(3-p-chlorobenzoylphenyl)-propionate is very near to 200 γ/kg and for [4'-(2',2'-dimethyl-1',3'-dioxolanyl)] methyl α-(3-p-chlorobenzoylphenyl)-propionate is between 1 and 2 mg/kg. The five compounds have an important analgesic activity.

C. Ulcerigenic activity

The ulcergenic activity was determined by a test inspired by Boissier et al. [Ther. Vol. 22 (1967), p. 157] using female rats 120-140 g which were starved for 24 hours before the start of the test. The products to be studied were orally administered as an aqueous suspension at a volume of 0.4 cc per 100 g of animal at varying doses. The animals were killed 7 hours after the treatment or 31 hours after the start of the starvation and the stomachs were recovered. The importance of the ulerous lesions were evaluated for each stomach, counting the number and size thereof. 2',3'-dihydroxypropyl 3-p-chlorobenzoylphenylacetate did not provoke the formation of ulcers at a dose of 200 mg/kg and neither did 2',3'-dihydroxypropyl 3-p-chlorobenzoyl-2-methyl-phenylacetate at a dose of 110 mg/kg. [4'-(2',2' dimethyl-1',3'-dioxolanyl)] methyl 3-p-chlorobenzoyl-2-methyl-phenylacetate did not provoke ulcers at a dose greater than 150 mg/kg and neither did 2',3'-dihydroxypropyl α-(3-p-chlorobenzoylphenyl) propionate at a dose greater than 100 mg/kg nor [4'-(2',2'-dimethyl-1',3'-dioxolanyl)] methyl α-(3-p-chlorobenzoylphenyl) propionate at a dose greater than 50 mg/kg.

Various modifications of the compositions and method of the invention may be made without departing from the spirit or scope thereof and it is to be understood that the invention is intended to be limited only as defined in the appended claims.

We claim:

1. A member of the group consisting of racemates and optically active isomers of benzoylphenylacetic acid esters of the formula $$\text{Cl}-\text{C}_6\text{H}_4-\text{CO}-\text{C}_6\text{H}_4-\text{CH(R)}-\text{COOCH}_2-\text{CH(OH)}-\text{CH}_2\text{OH}$$

wherein R is selected from the group consisting of hydrogen and alkyl of 1 to 7 carbon atoms, and each of the two benzene rings may be optionally substituted with a member of the group consisting of chlorine, fluorine, bromine, trifluoromethyl and alkyl and alkoxy and alkylthio of 1 to 7 carbon atoms in the alkyl portion.

2. A compound of claim 1 which is 2',3'-dihydroxypropyl 3-p-chlorobenzoylphenylacetate.

3. A compound of claim 1 which is 2',3'-dihydroxypropyl 3-p-chlorobenzoyl-2-methyl-phenylacetate.

4. A compound of claim 1 which is 2',3'-dihydroxypropyl α-(3-p-chlorobenzoylphenyl)-propionate.

5. An anti-inflammatory and analgesic composition comprising an effective amount of a compound of claim 1 and a pharmaceutical carrier.

6. A method of relieving pain and inflammation in warm-blooded animals which comprises administering to warm-blooded animals a safe and effective amount of a compound of claim 1.

* * * * *